(12) United States Patent
Tanaka et al.

(10) Patent No.: US 8,212,863 B2
(45) Date of Patent: Jul. 3, 2012

(54) SIGNAL OUTPUT BOARD AND ENDOSCOPE

(75) Inventors: Yasuhiro Tanaka, Machida (JP); Fumiyuki Okawa, Hino (JP); Hidenori Hashimoto, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 12/946,147

(22) Filed: Nov. 15, 2010

(65) Prior Publication Data

US 2011/0199472 A1   Aug. 18, 2011

Related U.S. Application Data

(63) Continuation of application No. PCT/JP2010/061336, filed on Jul. 2, 2010.

(30) Foreign Application Priority Data

Jul. 6, 2009   (JP) ................................. 2009-160020

(51) Int. Cl.
*H04N 7/12* (2006.01)
(52) U.S. Cl. ................................ 348/76; 348/65; 348/77
(58) Field of Classification Search .................... 348/65, 348/76, 77
See application file for complete search history.

(56) References Cited

U.S. PATENT DOCUMENTS

| | | | | |
|---|---|---|---|---|
| 5,047,847 | A * | 9/1991 | Toda et al. | 348/68 |
| 5,182,530 | A * | 1/1993 | Kelly et al. | 333/18 |
| 5,810,714 | A | 9/1998 | Takamura et al. | |
| 2005/0073589 | A1* | 4/2005 | Wakito | 348/207.99 |
| 2008/0064928 | A1 | 3/2008 | Otawara | |

FOREIGN PATENT DOCUMENTS

| | | |
|---|---|---|
| EP | 0 739 602 A1 | 10/1996 |
| EP | 1 834 575 A1 | 9/2007 |
| JP | 08-297250 | 11/1996 |
| JP | 2001-340289 | 12/2001 |
| JP | 2003-190086 | 7/2003 |
| JP | 2005-110740 | 4/2005 |
| JP | 2006-094955 | 4/2006 |
| JP | 2006-288759 | 10/2006 |
| WO | WO 2006/073186 A1 | 7/2006 |

OTHER PUBLICATIONS

International Search Report dated Aug. 3, 2010.

* cited by examiner

*Primary Examiner* — Jay Patel
*Assistant Examiner* — Geepy Pe
(74) *Attorney, Agent, or Firm* — Scully, Scott, Murphy & Presser, P.C.

(57) ABSTRACT

A signal output board includes: a drive signal generation section configured to generate a drive signal for a CCD; an inverse signal generation section configured to generate an inverse signal by inverting a phase of the drive signal from the drive signal generation section; a first signal transmission line portion configured to transmit the drive signal from the drive signal generation section; a second signal transmission line portion configured to transmit the inverse signal from the inverse signal generation section, at least part of the second signal transmission line portion being arranged in parallel to and adjacent to the first signal transmission line portion; an output end portion configured to output the drive signal transmitted by the first signal transmission line portion, to the outside; and an equivalent load section including a load equivalent to a transmission path for the drive signal from the output end portion to the electronic device, the equivalent load section being connected to an end portion of the second signal transmission line portion.

12 Claims, 6 Drawing Sheets

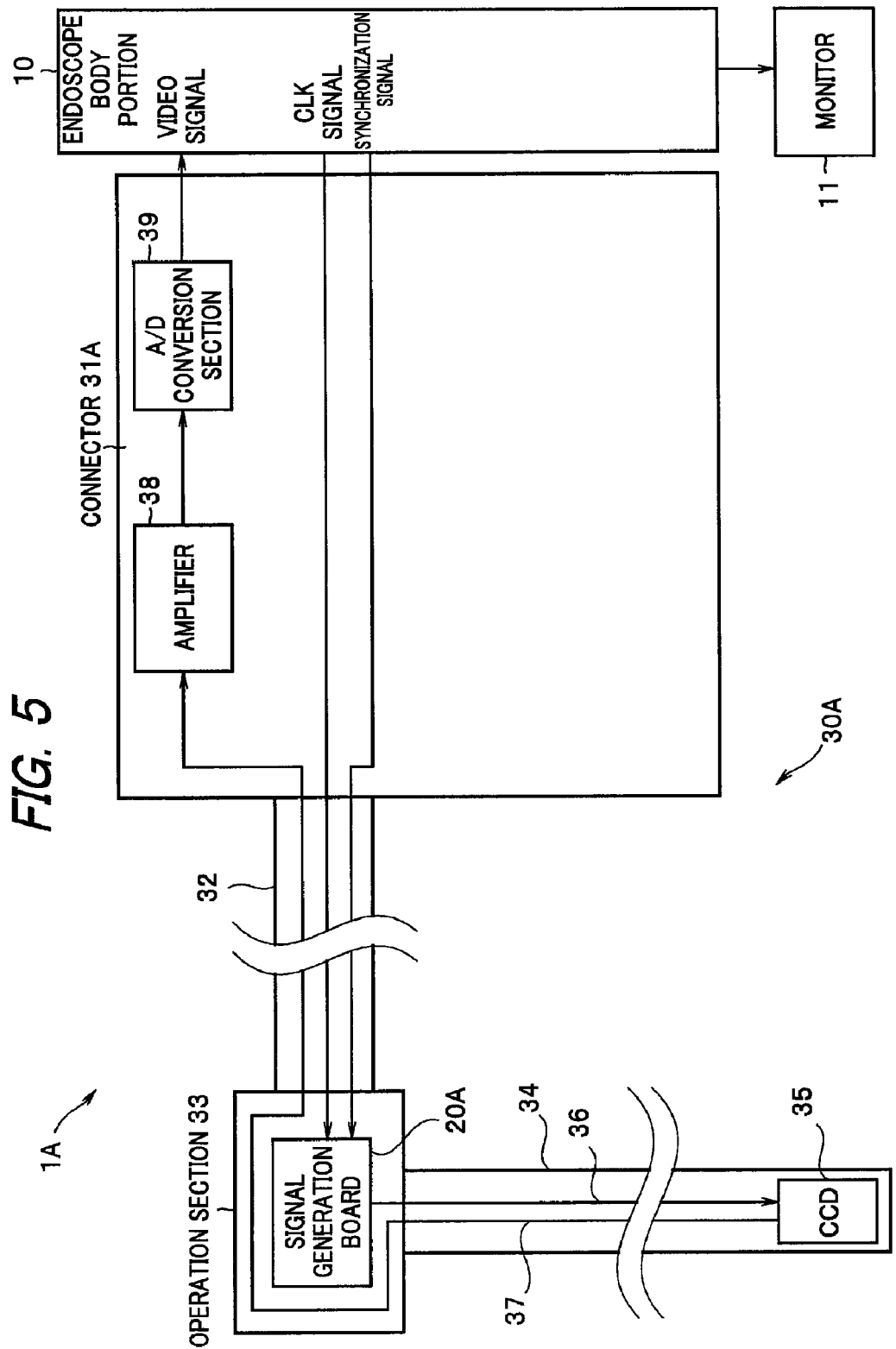

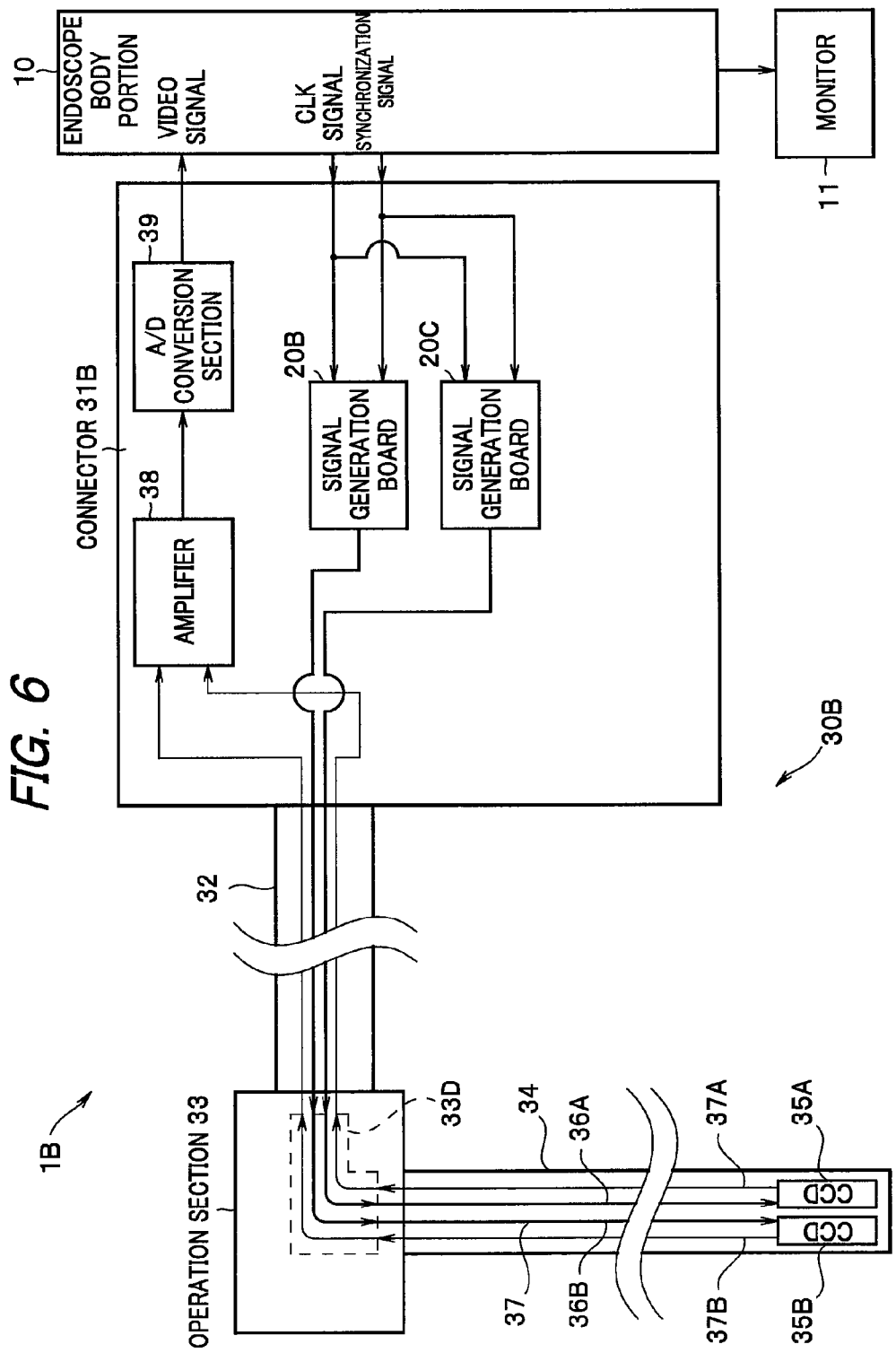

US 8,212,863 B2

SIGNAL OUTPUT BOARD AND ENDOSCOPE

CROSS REFERENCE TO RELATED APPLICATION

This application is a continuation application of PCT/JP2010/061336 filed on Jul. 2, 2010 and claims benefit of Japanese Application No. 2009-160020 filed in Japan on Jul. 6, 2009, the entire contents of which are incorporated herein by this reference.

BACKGROUND OF THE INVENTION

1. Field of the Invention

The present invention relates to a signal output board configured to output a drive signal for driving an electronic device, and an endoscope including the signal output board.

2. Description of the Related Art

In recent years, electronic endoscopes including a solid-state image pickup device, for example, a CCD, at a distal end of an insertion portion have widely been used in clinical sites. In an endoscope system including an electronic endoscope, a drive signal outputted from a signal output board is transmitted to a CCD provided at a distal end portion of an insertion portion via a cable, and a video signal from the CCD is transmitted to a camera control unit (hereinafter referred to as "CCU") configured to perform signal processing, whereby an endoscopic image is displayed on a monitor.

Meanwhile, there is concern that EMI (electromagnetic interference) noise, which is electromagnetic noise leaked from an electronic circuit, negatively affects the other electronic systems in the surroundings. Here, since a CCD uses a drive signal with a rectangular wave of several tens of megahertz, harmonic components and high-frequency components of the drive signal tend to be generated as electromagnetic waves, that is, EMI noise. In order to prevent malfunctions due to EMI noise in the clinical sites where various kinds of electronic devices are arranged, EMI noise occurrence is strictly regulated by the Medical Device Directive (MDD).

Accordingly, for example, Japanese Patent Application Laid-Open Publication No. 2001-340289 discloses an electronic endoscope with an end of a shield material covering a cable, which connects a CCD and a signal output board, electrically connected to an insertion portion-sheathing metal member in order to suppress EMI noise from the cable.

SUMMARY OF THE INVENTION

A signal output board according to an aspect of the present invention includes: a drive signal generation section configured to generate a drive signal for an electronic device; an inverse signal generation section configured to generate an inverse signal by inverting a phase of the drive signal from the drive signal generation section; a first signal transmission line portion configured to transmit the drive signal from the drive signal generation section; a second signal transmission line portion configured to transmit the inverse signal from the inverse signal generation section, at least part of the second signal transmission line portion being arranged in parallel to and adjacent to the first signal transmission line portion; an output end portion configured to output the drive signal transmitted by the first signal transmission line portion, to an outside; and an equivalent load section including a load equivalent to a transmission path for the drive signal from the output end portion to the electronic device, the equivalent load section being connected to an end portion of the second signal transmission line portion.

BRIEF DESCRIPTION OF THE DRAWINGS

FIG. 5 is a configuration diagram illustrating a configuration of an endoscope system including a signal output board according to a second embodiment.

FIG. 6 is a configuration diagram illustrating a configuration of an endoscope system including a signal output board according to a third embodiment.

DETAILED DESCRIPTION OF THE PREFERRED EMBODIMENT(S)

<First Embodiment>

Figure 1:
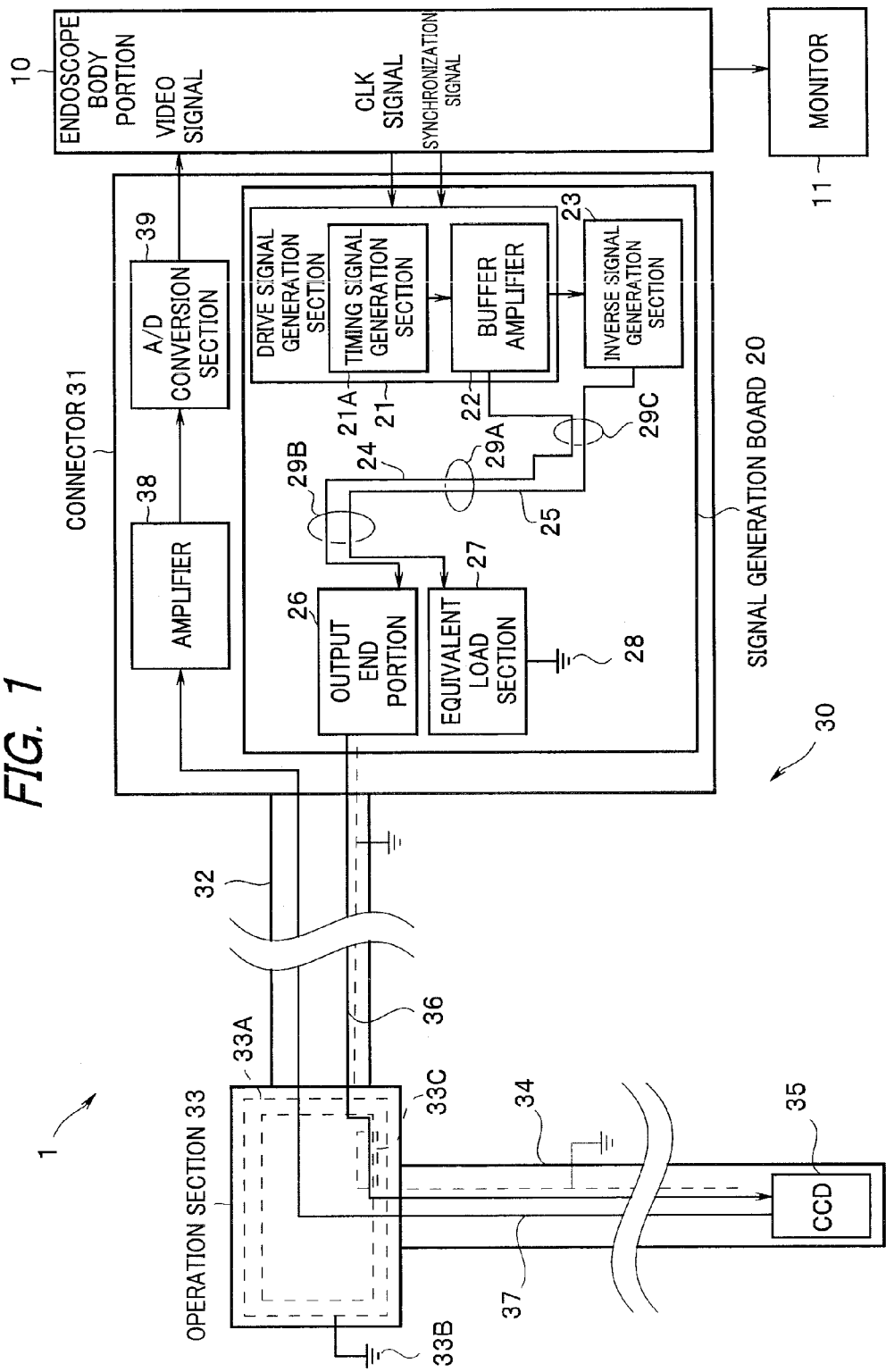
FIG. 1 is a configuration diagram illustrating a configuration of an endoscope system including a signal output board according to a first embodiment.

Hereinafter, an electronic endoscope 30 including a signal output board 20 according to a first embodiment of the present invention will be described with reference to FIGS. 1 to 3(B). As illustrated in FIG. 1 an endoscope system 1 includes an endoscope body portion 10, and an electronic endoscope 30 including a CCD 35, which is an electronic device detachably connected to the endoscope body portion 10. The endoscope body portion 10 includes a non-illustrated CCU (not illustrated) configured to process a video signal from the electronic endoscope 30, and display an endoscopic image on a monitor 11 connected to the endoscope body portion 10.

The electronic endoscope 30 includes an elongated insertion portion 34 to be inserted into a subject, an operation section 33 connected to the proximal end portion side of the insertion portion 34, a universal cord 32 connected to the operation section 33, and a connector 31 for attaching/detaching the universal cord 32 to/from the endoscope body portion 10. The insertion portion 34 includes a CCD 35, which is a solid-state image pickup device, at a distal end portion thereof. The operation section 33 is provided with a lever, a switch or the like for a user to operate the electronic endoscope 30, and includes a metal member 33A at a sheath portion thereof in order to reinforce the structure.

As illustrated in FIG. 1, the connector 31 includes a signal output board 20 configured to output a drive signal for driving the CCD 35, an amplifier 38 configured to amplify an analog video signal from the CCD 35, and an A/D conversion section 39 configured to convert the amplified analog video signal to a digital video signal and output the digital video signal to the CCU (not illustrated) in the endoscope body portion 10. At least one of the amplifier 38 and the A/D conversion section 39 may be arranged on the signal output board 20.

The signal output board 20 includes a drive signal generation section 21, an inverse signal generation section 23, a first signal transmission line portion 24, a second signal transmission line portion 25, an output end portion 26, an equivalent load section 27 and a ground portion 28.

The drive signal generation section 21 includes a timing signal generation section 21A and a buffer amplifier 22. The timing signal generation section 21A can be configured with an FPGA. The timing signal generation section 21A generates a timing signal from a clock signal and a synchronization signal from the endoscope body portion 10. The buffer amplifier 22 amplifies the timing signal to form a drive signal having a voltage according to the specifications of the CCD 35. If the specifications of the timing signal conform to the specifications of the CCD 35, the buffer amplifier 22 is not needed because the timing signal is used as a drive signal. The inverse signal generation section 23 generates an inverse signal by inverting a phase of the drive signal from the drive signal generation section 21.

The drive signal generation section 21 is drive signal generation means, the timing signal generation section 21A is timing signal generation means, the inverse signal generation section 23 is inverse signal generation section 23 means, and the buffer amplifier 22 is signal amplification means.

Although FIG. 1 illustrates the timing signal generation section 21A, the buffer amplifier 22 and the inverse signal generation section 23 as different components, the timing signal generation section 21A, the buffer amplifier 22 and the inverse signal generation section 23 may be configured with a CCD driver including one or two integrated circuit parts such as, e.g., buffer elements. Since a simple buffer cannot generate an inverse signal, an inverter is used for the inverse signal generation section 23. It should be noted that generating an inverted drive signal is generated in advance in the timing signal generation section 21A and using an inverter for the buffer amplifier 22 enables the inverse signal generation section 23 and the buffer amplifier 22 to be configured with one correction circuit part and thus, enables reduction of the circuit area.

The first signal transmission line portion 24 is a wiring configured to transmit the drive signal from the drive signal generation section 21 to the output end portion 26 configured to output the drive signal to the outside of the signal output board 20. The second signal transmission line portion 25 is a wiring configured to transmit the inverse signal from the inverse signal generation section 23 to the equivalent load section 27 or the ground portion 28. The output end portion 26 is connected to a cable 36 directly or via, e.g., another printed circuit board. The equivalent load section 27, which includes a load equivalent to a transmission load of a transmission path for a drive signal from the output end portion 26 to the CCD 35, for example, is an RC circuit in which a resistance and a capacitor are connected in series. The ground portion 28, which is an end portion having a ground potential, grounds an end portion of the second signal transmission line portion.

As schematically illustrated in FIG. 1, in the signal output board 20, the first signal transmission line portion 24 and the second signal transmission line portion 25 are arranged in parallel to and adjacent to each other at adjacent arrangement areas 29A, 29B and 29C, which are parts of the first signal transmission line portion 24 and the second signal transmission line portion 25.

Figure 2:
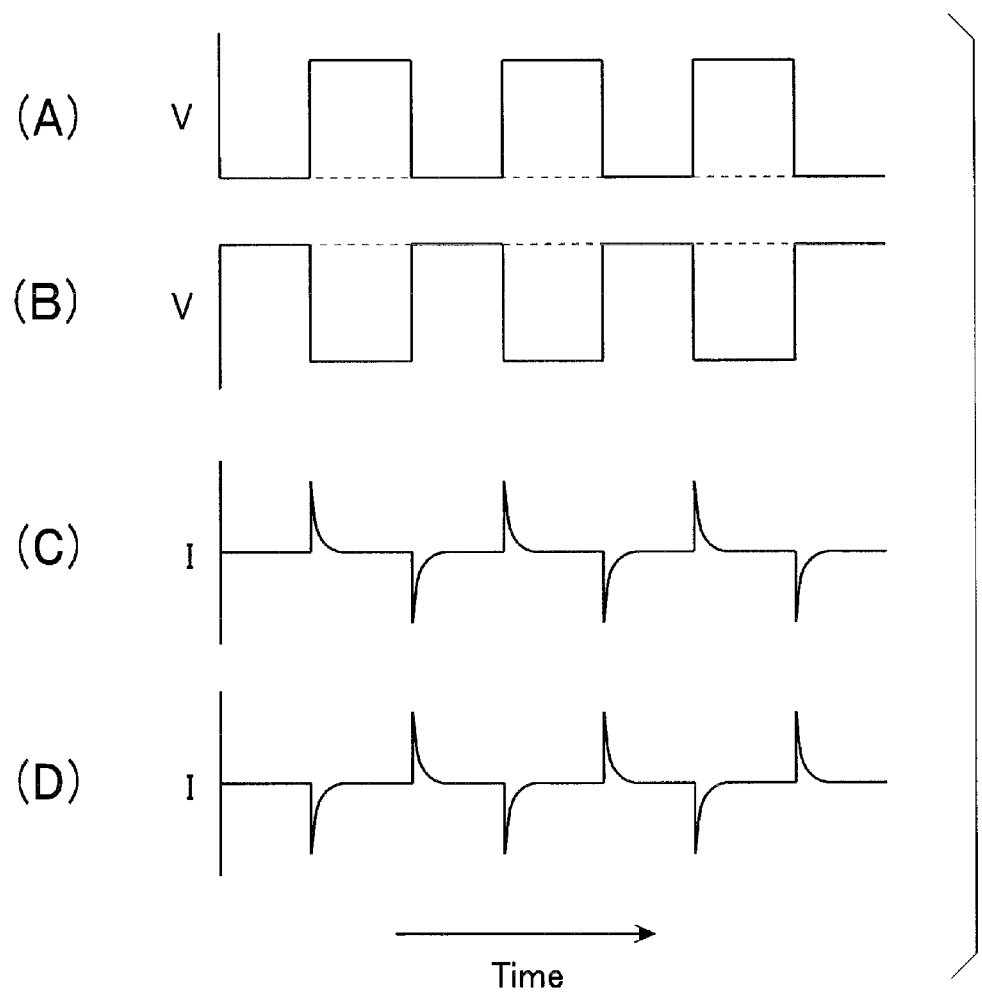
FIG. 2 is an illustration diagram for illustrating a relationship among a drive signal, an inverse signal, a current caused by generation of the drive signal, and a current caused by generation of the inverse signal in the signal output board according to the first embodiment.

Here, FIG. 2 is an illustration diagram illustrating a relationship among a drive signal (FIG. 2(A)), an inverse signal (FIG. 2(B)), a current caused by generation of the drive signal (FIG. 2(C)) and a current caused by generation of the inverse signal (FIG. 2(D)) in the signal output board 20 according to the present embodiment. The ordinate axes in FIGS. 2(A) and 2(B) represent voltages V, the ordinate axes in FIGS. 2(A) and 2(B) represent currents I, and the abscissa axes all represent time.

As illustrated in FIGS. 2(A) and 2(C), the drive signal generation section 21 generates an instantaneous current when generating a high-frequency rectangular-wave signal. The instantaneous current is one of the causes of EMI noise emitted by the signal output board 20. As illustrated in FIGS. 2(B) and (D), the inverse signal generation section 23 also generates an instantaneous current when generating a high-frequency rectangular-wave signal. The instantaneous current generated by the drive signal generation section 21 and the instantaneous current generated by the inverse signal generation section 23 have phases opposite to each other and thus, are mutually cancelled within the drive signal generation section 21. Consequently, the signal output board 20 enables reduction of EMI noise emitted to the outside.

As described above, the signal output board 20 does not cancel electromagnetic waves (EMI noise) emitted by the drive signal generation section 21 using electromagnetic waves emitted by the inverse signal generation section 23, but cancels a current that is the cause of the electromagnetic wave emission.

Accordingly, the drive signal generation section 21 and the inverse signal generation section 23 are preferably arranged not only on the same signal output board 20 but also adjacent to each other, and are more preferably configured with one integrated circuit. In particular, in the case of the signal output board 20 including the buffer amplifier 22, the buffer amplifier 22 and the inverse signal generation section 23 are preferably arranged adjacent to each other, and is particularly preferably configured with one integrated circuit. Furthermore, both are preferably circuits having same drive performance.

Here, in the signal output board 20, EMI noise may be emitted not only from the drive signal generation section 21, but also from the first signal transmission line portion 24 configured to transmit a drive signal. It may be difficult to shorten or linearly arrange the first signal transmission line portion 24 to reduce EMI noise from the first signal transmission line portion 24 because of the relationship with the other circuit component arrangement, which is not illustrated. However, in the signal output board 20, the first signal transmission line portion 24 and the second signal transmission line portion 25 are arranged in parallel to and adjacent to each other at the adjacent arrangement areas 29A to 29C, enabling reduction of EMI noise emitted from the first signal transmission line portion 24. In other words, the second signal transmission line portion 25, which is arranged in parallel to and adjacent to the first signal transmission line portion 24, generates electromagnetic waves having a phase opposite to the phase of electromagnetic waves generated by the first signal transmission line portion 24, and thus, the electromagnetic waves are mutually cancelled.

As described above, the signal output board 20 according to the present embodiment is a signal output board with EMI noise reduced. The effect of the signal output board 20 according to the present embodiment is particularly significant where the signal output board 20 is provided inside the connector 31, which cannot particularly easily be provided with a shield, among the electronic endoscope 30 components.

Figure 3A:
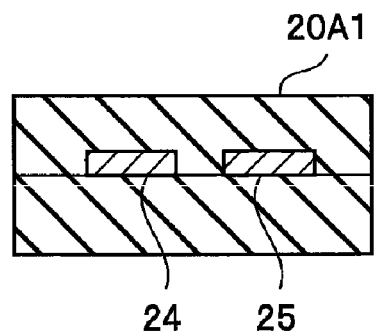
FIG. 3A is a schematic cross-sectional diagram for illustrating an arrangement of a first signal transmission line portion and a second signal transmission line portion of the signal output board according to the first embodiment, which indicates a case where the first signal transmission line portion and the second signal transmission line portion are arranged in parallel to and adjacent to each other in a plane.
Figure 3B:
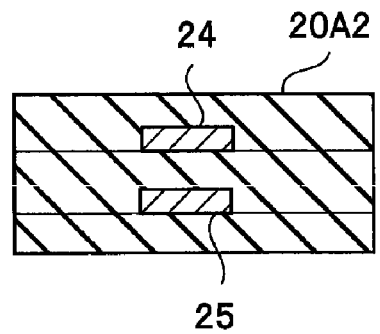
FIG. 3B is a schematic cross-sectional diagram for illustrating an arrangement of a first signal transmission line portion and a second signal transmission line portion of the signal output board according to the first embodiment, which indicates a case where the first signal transmission line portion and the second signal transmission line portion are arranged in parallel to and adjacent to each other in three dimensions.

As illustrated in FIG. 3A, where the first signal transmission line portion 24 and the second signal transmission line portion 25 are arranged in parallel to and adjacent to each other, the first signal transmission line portion 24 and the second signal transmission line portion 25 may be arranged on a conductor layer on a same plane of a signal output board 20A1, or as illustrated in FIG. 3B, the first signal transmission line portion 24 and the second signal transmission line portion 25 may also be three-dimensionally arranged on conductor layers in different planes of a signal output board 20A2, which is a multilayer printed circuit board. As a result of the three-dimensional arrangement of the first signal transmission line portion 24 and the second signal transmission line portion 25 on vertically-arranged conductor layers of a multilayer printed circuit board, the first signal transmission line portion 24 and the second signal transmission line portion 25 can be adjacently arranged more easily than the structure of FIG. 2(A), enabling more reliable reduction of EMI noise.

Furthermore, the signal output board 20 includes the equivalent load section 27. Although the equivalent load section 27 is not an essential component of the signal output board 20, in the signal output board 20 including the equivalent load section 27, the first signal transmission line portion 24 and the second signal transmission line portion 25 generate electromagnetic waves having a same intensity. In other words, the current value of a drive signal and the current value of an inverse signal become equal to each other, enabling electromagnetic waves resulting from the drive signal to be reliably cancelled by the electromagnetic waves resulting from the inverse signal.

Where a peaking circuit utilizing, e.g., LC resonance characteristics is provided in order to expand the frequency band of a drive signal, it is preferable to provide the peaking circuit between the drive signal generation section 21 and the inverse signal generation section 23.

Figure 4A:
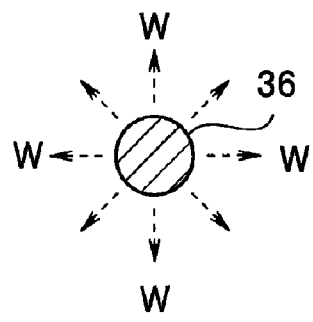
FIG. 4A is a schematic cross-sectional diagram for illustrating electromagnetic waves emitted from a cable, which indicates a case of a known electronic endoscope.

Here, as illustrated in FIG. 4A, in a known electronic endoscope, a shielded cable with its outer circumference portion covered by a shield member having a ground potential is used for a cable 36, but no special attentions are paid on providing the cable 36 in the operation section 33. Accordingly, electromagnetic waves W that not are blocked by the shield member are emitted from the cable 36 in all directions.

Figure 4B:
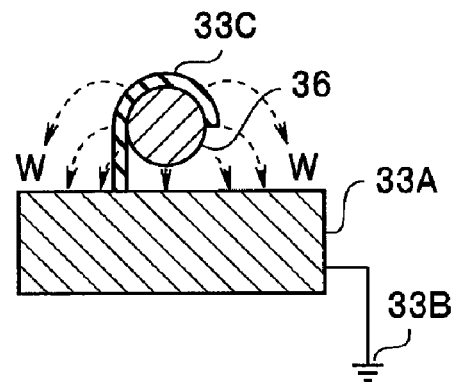
FIG. 4B is a schematic cross-sectional diagram for illustrating electromagnetic waves emitted from a cable, which indicates a case of an electronic endoscope including the signal output board according to the first embodiment.

Meanwhile, as illustrated in FIG. 1, in the electronic endoscope 30 in the endoscope system 1, the metal member 33A of the operation section 33 is made to have a ground potential by a ground portion 33B, and the cable 36 is arranged adjacent to the metal member 33A by means of a fixture 33C. It should be understood that a plurality of fixtures 33C may be provided. Consequently, as illustrated in FIG. 4B, in the electronic endoscope 30, a majority of the electromagnetic waves W emitted by the cable 36 is absorbed by the metal member 33A, enabling the level and variation of the EMI noise to be decreased.

Furthermore, the equivalent load section 27 and the ground portion 28, which are provided in the signal output board 20, may be provided in the operation section 33. In other words, the first signal transmission line portion 24 and the second signal transmission line portion 25 may be extended to the operation section 33 to transmit a drive signal from the operation section 33 to the CCD 35 via one cable. In this case, the first signal transmission line portion 24 and the second signal transmission line portion 25 are provided within the universal cord 32, requiring the universal cord 32 to be thick, which, however, is not a major problem because reduction in diameter of the universal cord 32 is less demanded than that of the insertion portion 34. The electronic endoscope with the above-described configuration enables reduction of EMI noise emitted from the universal cord 32, which results from a drive signal, while ensuring that the insertion portion 34 has a small diameter.

<Second Embodiment>

Next, an electronic endoscope 30A including a signal output board 20A according to a second embodiment of the present invention will be described with reference to FIG. 5. Since the electronic endoscope 30A according to the present embodiment is similar to the endoscope electronic endoscope 30 according to the first embodiment, components having the same functions as those of the first embodiment are provided with the same reference numerals as those of the first embodiment, and a description thereof will be omitted.

As illustrated in FIG. 5, an electronic endoscope 30A in an endoscope system 1A includes a signal output board 20A in the operation section 33. In other words, a CLK signal line and a synchronization signal line are extended to the operation section 33.

In FIG. 5, at least one of an amplifier 38 and an A/D conversion section 39, which are provided in a connector 31A, may be provided in the operation section 33.

Since the signal output board 20A according to the present embodiment has a configuration similar to that of the signal output board 20 according to the first embodiment, the signal output board 20A according to the present embodiment has an effect similar to that of the signal output board 20 according to the first embodiment. In other words, the signal output board 20A is a signal output board with EMI noise reduced. Furthermore, since the signal output board 20A is provided in the operation section 33, EMI noise emitted from the universal cord 32, which results from a drive signal, can be reduced.

<Third Embodiment>

Figure 7:
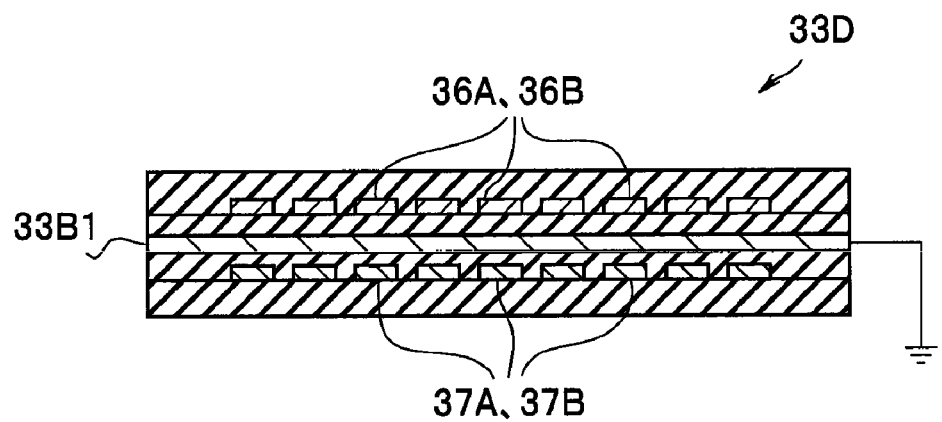
FIG. 7 is a schematic cross-sectional diagram illustrating a configuration of an FPC in an endoscope system including the signal output board according to the third embodiment.

Next, an electronic endoscope 30B including a signal output board 20B according to a third embodiment of the present invention will be described with reference to FIGS. 6 to 8. Since the electronic endoscope 30B according to the present embodiment is similar to the endoscope electronic endoscope 30 according to the first embodiment, components having the same functions as those of the first embodiment are provided with the same reference numerals as those of the first embodiment, and a description thereof will be omitted.

As illustrated in FIG. 6, an electronic endoscope 30B in an endoscope system 1B includes two CCDs 35A and 35B, and a signal output board 20B is provided together with another signal output board 20C configured to output a drive signal in a connector 31B. In other words, the electronic endoscope 30B includes two signal output boards 20B and 20C, each outputting a drive signal, and the drive signals are transmitted to the CCDs 35A and 35B via transmission lines 36A and 36B.

Since the signal output boards 20B and 20C each have components similar to those of the signal output board 20 according to the first embodiment, EMI noise can be reduced as in the signal output board 20.

Furthermore, it is preferable that the signal output board 20C output a drive signal having a phase that is the inverse of the phase of the drive signal outputted by the signal output board 20B, which can reduce not only EMI noise in the connector 31B but also EMI noise generated from a cable 36.

Where each of the CCDs 35A and 35B needs a drive signal and an inverse signal, the CCDs 35A and 35B can mutually share a drive signal and an inverse signal.

Furthermore, as illustrated in FIG. 6, in the electronic endoscope 30B, for improvement in ease of assembly, drive signals and video signals are transmitted using a flexible printed circuit board (FPC) 33D in the operation section 33. As illustrated in FIG. 7, in the FPC 33D, transmission lines 36A and 36B for drive signals and transmission lines 37A and 37B for video signals are separated by a conductor layer 33B1 having a ground potential. Consequently, the transmission lines 37A and 37B for video signals are not negatively affected by crosstalk from the transmission lines 36A and 36B for drive signals.

Figure 8:
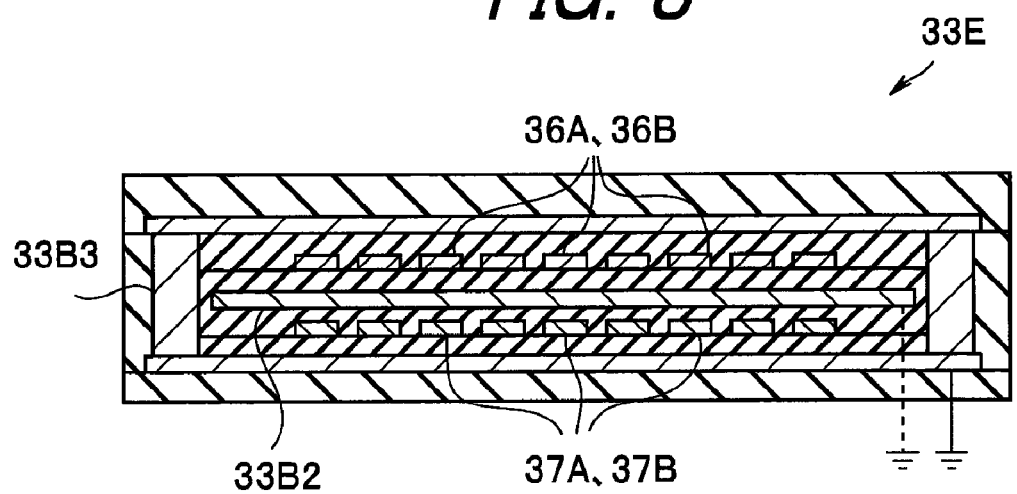
FIG. 8 is a schematic cross-sectional diagram illustrating a configuration of an FPC in an endoscope system including the signal output board according to the third embodiment.

Furthermore, covering the transmission lines 37A, 37B, 36A and 36B with a conductor 33B3 having a ground potential, like a FPC 33E, which is illustrated in FIG. 8, enables reduction of EMI noise emitted from the FPC 33E.

Although in the above description, the present invention has been described taking a drive signal output board in an electronic endoscope system including a CCD as an electronic device, as an example, the present invention can provide its effect for any signal output board configured to generate a high-frequency signal, in particular, a rectangular-wave high-frequency signal, which has the problem of EMI noise. For example, the present invention can be used for a signal output board configured to generate a drive signal for driving an electronic surgical knife or manipulator as an electronic device.

Furthermore, for a signal output board configured to generate a plurality of different drive signals, an inverse signal generation section may be provided for each drive signal generation section, or an inverse signal generation section may be provided only for a drive signal generation section particularly requiring noise reduction.

The present invention is not limited to the above-described embodiments, and various modifications and alternations or the like of the present invention can be made without departing from the scope and spirit of the present invention.

What is claimed is:

1. A signal output board comprising:
    a drive signal generation section configured to generate a drive signal for an electronic device;
    an inverse signal generation section configured to generate an inverse signal by inverting a phase of the drive signal from the drive signal generation section;
    a first signal transmission line portion configured to transmit the drive signal from the drive signal generation section;
    a second signal transmission line portion configured to cancel noise emitted by the first signal transmission line portion by transmitting the inverse signal from the inverse signal generation section along at least a part of the second signal transmission line portion arranged in parallel with and adjacent to the first signal transmission line portion;
    an output end portion configured to output the drive signal transmitted by the first signal transmission line portion to an outside; and
    an equivalent load section including a load equivalent to a transmission path for the drive signal from the output end portion to the electronic device, the equivalent load section being connected to an end portion of the second signal transmission line portion.

2. The signal output board according to claim 1, wherein the second signal transmission line portion is arranged in parallel to and adjacent to the first signal transmission line portion at a plurality of positions.

3. The signal output board according to claim 1,
    wherein the signal output board includes a multilayer printed circuit board including a plurality of conductor layers; and
    wherein the second signal transmission line portion is arranged in a three-dimensional manner on a different conductor layer from the conductor layer on which the first signal transmission line portion is arranged.

4. The signal output board according to claim 1, wherein the drive signal generation section includes a timing signal generation section configured to generate a timing signal, and a signal amplification section configured to amplify the timing signal.

5. The signal output board according to claim 1, wherein the transmission path for the drive signal from the output end portion to the electronic device includes a cable.

6. The signal output board according to claim 1, wherein the electronic device includes a solid-state image pickup device provided at a distal end portion of an electronic endoscope; and the signal output board is provided inside a connector of the electronic endoscope, the connector being connected to an electronic endoscope body portion.

7. The signal output board according to claim 6, wherein the electronic endoscope includes a metal member having a ground potential in an operation section, and the cable is arranged adjacent to the metal member.

8. The signal output board according to claim 1,
    wherein the electronic device includes a solid-state image pickup device provided at a distal end portion of an electronic endoscope; and
    wherein the signal output board is provided in an operation section of the electronic endoscope.

9. The signal output board according to claim 6,
    wherein the electronic endoscope includes a plurality of the solid-state image pickup devices; and
    wherein the signal output board is provided together with another signal output board configured to output the drive signal.

10. The signal output board according to claim 9, wherein the signal output board outputs a drive signal having a phase that is an inverse of a phase of the drive signal outputted by the other signal output board.

11. The signal output board according to claim 1, comprising a ground portion configured to ground the equivalent load section.

12. An endoscope comprising:
    an insertion portion including an image pickup device at a distal end portion thereof;
    an operation section;
    a universal cord;
    a connector; and
    a signal output board comprising:
        a drive signal generation section configured to generate a drive signal for an electronic device;
        an inverse signal generation section configured to generate an inverse signal by inverting a phase of the drive signal from the drive signal generation section;
        a first signal transmission line portion configured to transmit the drive signal from the drive signal generation section;

a second signal transmission line portion configured to cancel noise emitted by the first signal transmission line portion by transmitting the inverse signal from the inverse signal generation section along at least a part of the second signal transmission line portion arranged in parallel with and adjacent to the first signal transmission line portion;

an output end portion configured to output the drive signal transmitted by the first signal transmission line portion to an outside; and an equivalent load section including a load equivalent to a transmission path for the drive signal from the output end portion to the electronic device, the equivalent load section being connected to an end portion of the second signal transmission line portion, wherein the signal output board is disposed in the operation section or the connector.

* * * * *